United States Patent [19]

Larock et al.

[11] Patent Number: 5,169,959

[45] Date of Patent: Dec. 8, 1992

[54] FREE RADICAL-CATALYZED SYNTHESIS OF BENZOPROSTACYCLINS

[75] Inventors: Richard C. Larock, Ames, Iowa; Nam H. Lee, Urbana, Ill.

[73] Assignee: Iowa State University Research Foundation, Inc., Ames, Iowa

[21] Appl. No.: 764,181

[22] Filed: Sep. 23, 1991

[51] Int. Cl.[5] .......................................... C07D 307/93
[52] U.S. Cl. .................................................... 549/458
[58] Field of Search ........................................ 549/458

[56] References Cited

U.S. PATENT DOCUMENTS

| | | | |
|---|---|---|---|
| 4,230,879 | 10/1980 | Wissner et al. | 560/121 |
| 4,301,164 | 11/1981 | Ohno et al. | 549/458 |
| 4,474,802 | 10/1984 | Ohno et al. | 549/458 |
| 4,590,014 | 5/1986 | Wolf et al. | 260/502.4 |

OTHER PUBLICATIONS

*Aldrichimica Acta*, Aldrich Chemical Co. Inc., Milwaukee, WI (publisher), vol. 16, at p. 14, (1983).
T. Bargar et al., *J. Med. Chem.*, 29, 313 (1986).
W. Bartmann et al., *Agnew. Chem. Int. Ed. Eng.*, 21, 751 (1982).
G. Born, *Nature*, 194, 927 (1962).
D. Deardorff et al., *Tetrahedron Lett.*, 26, 5615 (1984).
J. Fried et al., *Ann. N.Y. Acad. Sciences*, 38, 180 (1971).
R. Johnson et al., *Prostaglandins*, 12, 915 (1976).
M. Jung et al., *Tetrahedron Lett.*, 23, 3851 (1982).
G. Keck et al., *J. Org. Chem.*, 52, 2958 (1987).
R. Larock et al., *Tetrahedron Lett.*, 43, 2013 (1987).
M. Midland et al., *Organic Synthesis*, 63, 57 (1984).
S. Moncada et al., *Nature*, 263, 663 (1976).
H. Nagase et al., *Tetrahedron Lett.*, 31, 4493 (1990).
R. Newton et al., *Synthesis*, 449 (1984).
R. Noyori et al., *J. Am. Chem. Soc.*, 106, 6717 (1984).
M. Ochiai et al., *Tetrahedron Lett.*, 24, 4025 (1983).
K. Ohno et al., *Tetrahedron Lett.*, 31, 4485 (1990).
K. Parker et al., *Tetrahedron Lett.*, 27, 2833 (1986).
G. Russell et al., *J. Am. Chem. Soc.*, 106, 4622 (1984).
G. Russell et al., *Organometallics*, 7, 696 (1988).
K. Shankaran et al., *Tetrahedron Lett.*, 26, 6001 (1985).
W. Skubala, *J. Med. Chem.*, 29, 313 (1986).
C. Sloan et al., *Tetrahedron Lett.*, 29, 4685 (1988).
J. Stille, *Agnew. Chem. Int. Ed. Engl.*, 25, 508 (1986).
G. Stork et al., *J. Am. Chem. Soc.*, 108, 6385 (1986).
M. Suzuki et al., *Tetrahedron*, 46, 4809 (1990).
T. Umetsu et al., *Japan J. Pharmacol.*, 43, 81 (1987).
C. Walling, *Tetrahedron Symp.*, 41, 3887 (1985).
Larock and Lee, J. Org. Chem., vol. 56, pp. 6253–6254 (1991).

*Primary Examiner*—Bernard Dentz
*Attorney, Agent, or Firm*—Merchant, Gould, Smith, Edell, Welter & Schmidt

[57] ABSTRACT

A method is provided for preparing benzoprostacyclins by the free-radical-catalyzed tandem alkene insertion into a 1,4-bisoxy-substituted cyclopent-2-ene intermediate.

17 Claims, No Drawings

FREE RADICAL-CATALYZED SYNTHESIS OF BENZOPROSTACYCLINS

BACKGROUND OF THE INVENTION

Prostacyclin (I, PGI$_2$), first discovered in 1976, is one of the most potent natural inhibitors of blood platelet aggregation. (See S. Moncado et al., *Nature*, 263, 663 (1976) and R. Johnson et al., *Prostaglandins*, 12, 915 (1976)). Unfortunately, its low metabolic stability due to enol ether hydrolysis greatly diminishes its pharmacological utility. Major interest of late has focused on the synthesis of more stable analogs, such as the benzoprostacyclins Ia-c, described by K. Ohno et al. in U.S. Pat. No. 4,301,164.

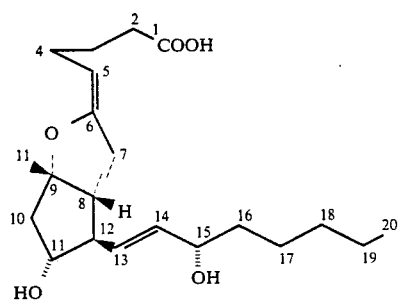

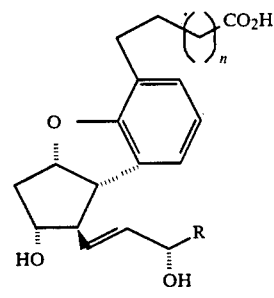

| n | R |
|---|---|
| Ia | 1 | n-C$_5$H$_{11}$ |
| Ib | 1 | CH(Me)CH$_2$C≡CCH$_3$ |
| Ic | 0 | n-C$_5$H$_{11}$ |

These compounds similarly exhibit substantial inhibition of platelet aggregation.

Present synthetic approaches to the benzoprostacyclins are very lengthy and rather inefficient. For example, the synthesis of compound Ia as reported by H. Nagase et al., *Tetrahedron Lett.*, 31, 4493 (1990) requires steps. As reported by K. Ohno et al. in U.S. Pat. No. 4,474,802, the synthesis of the C$_1$-methyl ester of Ib requires at least 17 steps.

Therefore, a need exists for efficient methods to synthesize benzoprostacyclins.

SUMMARY OF THE INVENTION

The present invention provides a method for the synthesis of benzoprostacyclins of general formula II.

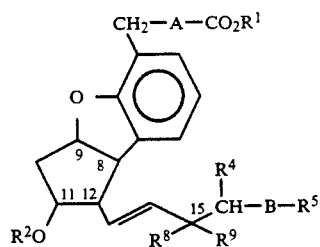

wherein R$^1$ is a pharmaceutically acceptable cation, H or (C$_1$-C$_{12}$)alkyl, preferably (C$_1$-C$_4$)alkyl; R$^2$ is H, (C$_1$-C$_{12}$)-alkyl, (C$_1$-C$_{10}$)acyl or (C$_7$-C$_{13}$)aroyl; R$^8$ is H or (C$_1$-C$_{12}$)alkyl, and R$^9$ is OR$^3$ wherein R$^3$ is H, (C$_1$-C$_{12}$)alkyl, (C$_1$-C$_{10}$)acyl, or (C$_7$-C$_{13}$)aroyl; or R$^8$ and R$^9$ taken together are keto; R$^4$ is H, F, methyl or ethyl; R$^5$ is (C$_1$-C$_5$)alkyl; A is —CH$_2$—, —O—CH$_2$—, —CH$_2$—CH$_2$— or —CH=CH—, and B is —(CH$_2$)$_n$—Z— wherein n is 0-4 and Z is —CH$_2$—CH$_2$—, —CH=CH— or —C≡C—.

In compound II, the bonds at cyclopentane ring positions 8, 9, 11 and 12, individually are in either the alpha (extending below the plane of the cyclopentane ring, indicated by a broken line) or beta (extending above the plane of the cyclopentane ring, indicated by a wedged line) configuration, with the "natural" configuration shown for I. The natural or corresponding inverted configurations at C$_{15}$ may be either (R) or (S). Preferably, the C$_8$ and C$_9$ cyclopentane ring bonds are both alpha (the "natural" configuration) or both beta.

Two novel compounds which can be prepared in accord with the present method wherein R$^1$, A, R$^2$, R$^3$, R$^4$, B and R$^5$ are as described hereinabove, are depicted below (IIa, IIb).

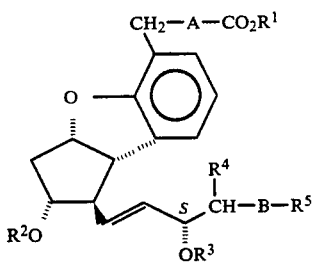

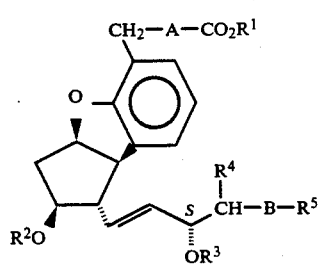

Representative compounds of formula II, wherein A=—CH$_2$—CH$_2$—, R$^2$=R$^3$=R$^4$=H, B=—(CH$_2$)$_3$— and R$^5$=CH$_3$, which were prepared in accord with the present method are listed in Table I, below.

TABLE I

| Compound No. | Benzoprostacyclin Analogs Bond Orientation | | | | |
|---|---|---|---|---|---|
| | $C_8$ | $C_9$ | $C_{11}$ | $C_{12}$ | $C_{15}$—OH |
| 11 ($R^1$ = Et) | α | α | α | β | $C_{15}$=O |
| 12 ($R^1$ = Et) | α | α | α | β | α |
| 13 ($R^1$ = Et) | α | α | α | β | β |
| 15 ($R^1$ = Et) | β | β | β | α | α |
| 12 ($R^1$ = H) | α | α | α | β | β |
| 15 ($R^1$ = H) | β | β | β | α | α |

The present method employs intermediate III in the present synthetic method:

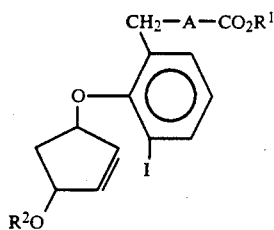

(III)

wherein $R^1$ is ($C_1$-$C_{12}$) alkyl and A and $R^2$ are as defined above. Preferably, the 1,4-cyclopentenyloxy bonds are both alpha, $R^2$ is H, and $R^1$ is ($C_1$-$C_4$)alkyl.

As used herein, the term "alkyl" includes branched or straight-chain alkyl groups, or ($C_3$-$C_{12}$)cycloalkyl, preferably ($C_3$-$C_6$)cycloalkyl. Aroyl is preferably ($C_7$-$C_{11}$)aroyl, e.g., benzoyl or naphthoyl, wherein the aryl ring is either unsubstituted or is substituted with 1-4 ($C_1$-$C_4$)alkyl or 1-4 ($C_1$-$C_4$)alkoxy groups. The preferred acyl is acetyl. Preferably A and B are methylene (—$CH_2$—) or ethylene (—$CH_2$—$CH_2$—). Preferred pharmaceutically-acceptable cations are alkali metal salts, $NH_4^+$, or the carboxylic acid addition salts of non-toxic amines.

In accord with the present method, a compound of the formula III, wherein $R^2$ is as defined above, and preferably is H; $R^1$ is as defined above, and preferably is ($C_1$-$C_{12}$)alkyl and A is as defined above, and preferably is —$CH_2$— or —$CH_2$—$CH_2$—, is reacted with a compound of the formula IV:

$$R^7—CH=CH—C(O)—CH(R^4)—B—R^5 \quad \text{IV}$$

wherein $R^7$ is tris($C_1$-$C_4$)alkylSn or (phenyl)$_3$Sn; $R^4$, B and $R^5$ are as described hereinabove; in the presence of a catalytic amount of a free radical source to directly yield the corresponding compound of formula II wherein $R^8$ and $R^9$ taken together are keto. Preferably, the reaction is carried out in the presence of an organic solvent, and the free radical addition is thermally initiated, e.g., at about 50°-150° C.

The $C_{15}$-keto group of compound II can then be reduced to the corresponding $C_{15}$-hydroxy group by methods known to the art to yield compounds of formula II wherein $R^8$ is H or ($C_1$-$C_{12}$)alkyl and $R^9$ is OH. Optionally, the moiety —CH=CH—C(O)—CH($R^4$)—B—$R^5$ in compound IV can be replaced by the moiety —CH=CH—CH($OR^3$)—CH($R^4$)—B—$R^5$ by reaction of the intermediate III with a compound of formula V:

$$R^7—CH=CH—C(R^8)(OR^3)—CH(R^4)B—R^5 \quad . \text{V}$$

wherein $R^8$ is H or ($C_1$-$C_{12}$)alkyl and $R^3$, $R^4$, $R^5$, $R^7$ and B are as described above, in the presence of a catalytic amount of a free radical source, e.g., under essentially the same reaction conditions used to form $C_{15}$-keto II. Preferably, $R^3$ is H, and the $C_3$-configuration is fixed, so that a $C_{15}$-S or $C_{15}$-R prostacyclin results. In either case, the $C_1$-ester can then be saponified if necessary, to yield compounds of formula II wherein $R^1$ is H, and the $CO_2H$ group can also be converted into a pharmaceutically-acceptable carboxylate salt.

The moiety —CH=CH— may be cis or trans. It is preferably trans in compound IV, and cis in moieties A and B in compounds II or III.

DETAILED DESCRIPTION OF THE INVENTION

The preparation of a preferred embodiment of intermediate III is summarized in Scheme 1.

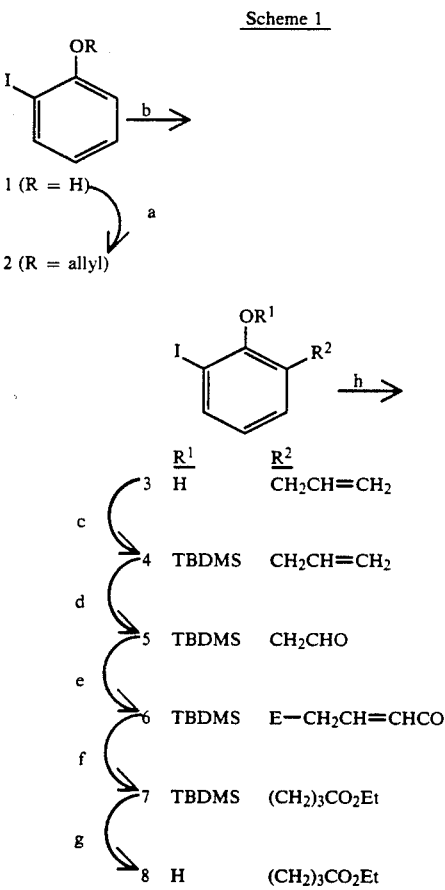

Scheme 1

Steps (a)–(g) are summarized in Table II below, wherein the numbers preceding the reactants are mole ratios: 1 mole of 1-8, unless otherwise noted.

TABLE II

| | Synthesis of Compound 9 | |
|---|---|---|
| Step | Reactants | Yield |
| a | 1,2 allyl bromide, 1.2 K$_2$CO$_3$, acetone | 94% |
| b | 0.8 MeAlCl$_2$, −20° C. | 70% |
| c | t-butyldimethylsilyl chloride, imidazole | 90% |
| d | ozone, −78° C./Me$_2$S | 83% |
| e | Ph$_3$P=CHCO$_2$Et | 83% |
| f | H$_2$, cat. PtO$_2$ | 90% |
| g | n-Bu$_4$NF | 94% |
| h | 1,5-cyclopentadiene monoepoxide, 2% Pd(PPh$_3$)$_4$, THF | 72% |

The requisite regio- and stereochemistry is efficiently introduced by the palladium-catalyzed opening of a vinylic epoxide. See, D. R. Deardorff et al., Tetrahedron Lett., 26, 5615 (1984).

The reaction of 9 with trans-1-(tri-n-butylstannyl)-oct-1-en-3-one (10) and azobisisobutyronitrile (AIBN), in a mole ratio to 9 of 4:0.1, respectively, proceeded in 80% yield at 90° C. in toluene to give compound 11, as shown in Scheme 2, below.

Scheme 2

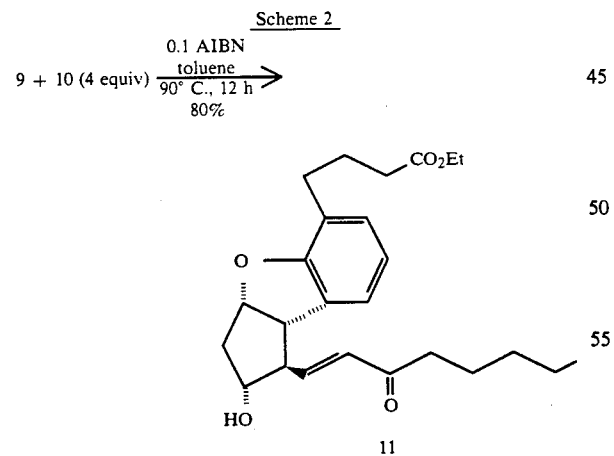

Mechanistically, this process is believed to involve formation of a aryl radical of 9 that in turn self-adds to produce a free radical at nascent position 12. This active species reacts in situ across the C—Sn bond of 10 to yield 11.

(S)-BINAL-H reduction of enone 11 in accord with the procedure of R. Noyori et al., J. Amer. Chem. Soc., 106, 6717 (1984), was unselective, affording a mixture of diastereomers 12 (R=Et) and 13 (R=Et) in a ratio of about 1:5, in accord with Scheme 3, below.

Scheme 3

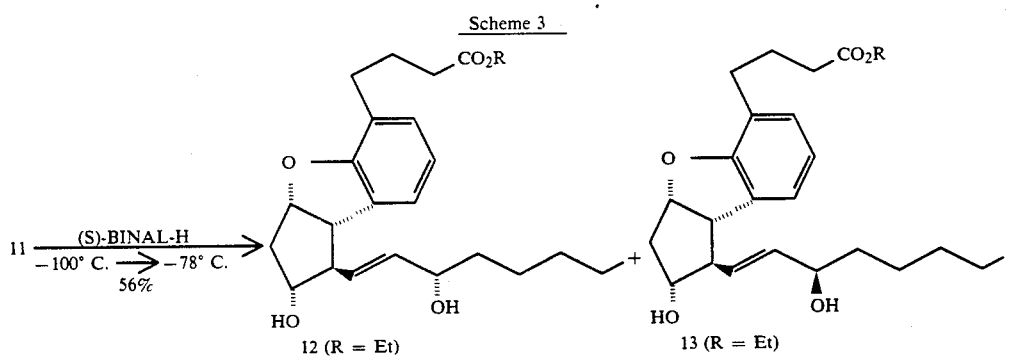

A more direct approach to the desired 15-(S) isomer used the chiral γ-stannyl allylic alcohol 14, although few such unactivated vinylic stannanes appear to have previously been used as a radical trap. See, for example, G. A. Russell et al., J. Amer. Chem. Soc., 106, 4622 (1984) and G. A. Russell et al., Organometallics, 7, 696 (1988). Compound 14 was prepared as described by M. Suzuki et al., Tetrahedron, 46, 4809 (1990).

Scheme 4

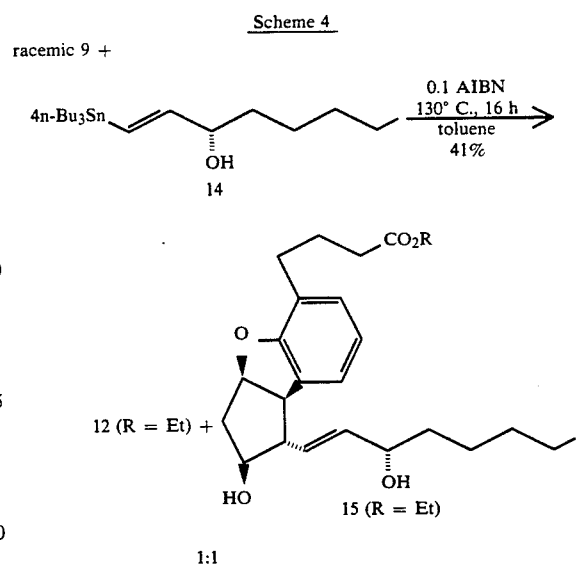

A 1:1 mixture of diastereomers cleanly separable by flash chromatography was obtained in 41% overall yield. Separation and hydrolysis afforded the corresponding chiral benzoprostacyclins 12 (R=H) and 15 (R=H) in 72% and 74% yields respectively.

In carrying out the synthesis of the compound of formula II, the aryl iodide III is preferably combined with an excess of compound IV, e.g., preferable in a mole ratio of III:IV of about 1:1.25–20, in a suitable organic solvent which is relatively inert to free radical species, i.e., in benzene, toluene, xylene and the like. The reaction mixture is preferably stirred at about 50°–150° C. for about 5–48 hr. under an inert atmosphere, with an effective catalytic amount of a source of free radicals, or "free radical initiator." Useful free radical initiators include AIBN, azobiscyclohexylnitrile, benzoyl peroxide, other aroyl peroxides and the like. For other useful free radical sources, see U.S. Pat. No. 4,590,014, the disclosure of which is incorporated herein by reference, and C. C. Walling, *Tetrahedron Symp.*, 41, 3887 (1985). The crude product is extracted, i.e., into ethyl acetate and can be purified by chromatography.

Compounds of formula V, wherein $R^7$ is a trialkylstannyl group, $R^8$ is H and $R^9$ is $OR^3$ can be prepared as disclosed by J. K. Stille, in Angew. Chem. Int. Ed. Engl., 25, 508 (1986), M. Ochiai et al., *Tet. Letters*, 24, 4025 (1983), and by G. Keck et al., *J. Org. Chem.*, 52, 2958 (1987). For example tri-n-butyltin hydride can be reacted with a protected 3-hydroxy-1-alkyne as disclosed in U.S. Pat. No. 4,230,879. Compounds of formula IV, wherein $R^7$ is a trialkylstannyl group, and $R^8$ and $R^9$ taken together are keto, e.g., 10, can be prepared as disclosed by W. Bartmann et al., *Angew. Chem. Int. Ed. Engl.*, 21, 751 (1982); R. F. Newton et al., *Synthesis*, 449 (1984) and W. Skuballa, *J. Med. Chem.*, 29, 313 (1986).

The reduction of $C_{15}$-keto-benzoprostacyclins to yield compounds of formula II, wherein $R^3 = H$ can be accomplished with borohydride reducing agents such as zinc borohydride or sodium borohydride, or with chiral reducing agents such as lithium aluminum hydride/α,α-binaphthol ((S)-BINAL-H), as described in detail in the working Examples, below and in *Aldrichimica Acta*, 16, 14 (1983). The free $Cu_{11}$-OH or $C_{15}$-OH groups can then be acylated or aroylated by conventional methodologies, e.g., via reaction with anhydrides or acid chlorides in the presence of an organic base. Compounds of formula II wherein $R^1$ is alkyl can be converted into the corresponding carboxylic acids by saponification with alkali metal hydroxides in alcoholic solvents followed by neutralization of the reaction mixture. Pharmaceutically-acceptable cations ($R^1$) include alkali metal salts and the amine salts disclosed in K. Ohno. et al. (U.S. Pat. No. 4,474,802), which is incorporated by reference herein.

The reaction methodology employed to prepare compound 9, as outlined in Scheme 1, can be readily modified to prepare other aryl iodides of general formula III, e.g., by the use of aldehydes of varying chain length in step (e). Compound III wherein A is CH=CH and $R^2$ is H is readily prepared by deprotecting compound 6, e.g., via step (g).

Bioassays

The compounds prepared by the present method exhibit potent platelet aggregation inhibiting activity and blood pressure decreasing activity by vasodilation. The efficacy of the compound to inhibit platelet aggregation is examined according to Born's method (*Nature*, 194, 927 (1962)). The blood is collected from humans or anesthetized rabbits. The blood is anti-coagulated with a 3.8% aqueous solution of sodium citrate in an amount of a tenth volume of the blood and centrifuged for 10 minutes at 200×g to obtain platelet rich plasma. After pretreatment of the platelet rich plasma with the benzoprostacyclin, aggregation is measured by aggregometer with arachidonic acid, adenosine-2-phosphate(ADP) or collagen as the aggregation inducer. It is shown that compounds 11 (R=Et), 12 (R=H or Et), 13 (R=Et), and 15 (R=H or Et) exhibit potent inhibitory activity.

To examine the efficacy of a benzoprostacyclin to reduce blood pressure, the blood pressure of the carotid artery of rats under pentobarbital anesthesia is measured. The compounds listed above are injected into the vein through an indwelling catheter. These compounds exhibit substantially the same activity as prostaglandin $E_1$ at the same dose of 0.05 to 100 μg/kg and have a longer duration of action than prostaglandin $E_1$.

An anti-thrombotic agent containing any of these benzoprostacyclins as the active component may be applied to prevent clotting in extracorporeal circulation, treatment of a disturbance of peripheral circulation such as Buerger's disease and Raynaud's disease, prevention and treatment of myocardial infarction, angina pectoris and cerebral infarction, prevention of TIA, treatment of diabetic thrombosis and prevention and treatment of arteriosclerosis.

For the treatment of Buerger's disease, the pharmacologically effective intravenous dose of a compound of the invention is 0.001 to 100 μg/kg/min. In case of using the compound as an anti-thrombotic agent, 0.001 to 50 mg of the compound is orally administered to a patient one to three times a day, and in case of using the compound as a blood pressure-reducing agent, 0.01 to 50 mg of the compound is orally administered to a patient one to three times a day.

The benzoprostacyclins can be orally administered as a form of a solid substance containing excipients such as starch, lactose, and sucrose, or can be parenterally administered in a form of a sterilized aqueous solution. Such a solution may contain another solute, for instance, glucose or sodium chloride in an amount sufficient to make the solution isotonic. Various preparations for oral administration, injections, infusions, eye drops and suppositories can be prepared.

The invention will be further described by reference to the following detailed examples.

EXAMPLE 1

Preparation of Compound 2

A solution of o-iodophenol (6.6 g, 30 mmol), allyl bromide (4.0 g, 33 mmol) and potassium carbonate (4.6 g, 3.3 mmol) in 7.5 ml of acetone was refluxed for 8 hr. The reaction mixture was diluted with 40 ml of water, and extracted with ether (2×25 ml). The organic phase was washed with brine (25 ml), and then dried over $MgSO_4$. Concentration, followed by flash chromatography, gave compound 2 as a colorless oil: 6.8 g, 94% yield, $^1H$ NMR ($CDCl_3$) δ 7.77 (dd, J=17.4 and 10.5 and 7.8 Hz, 1.5 Hz, 1 H, Ar), 7.27 (dt, J=1.8 and 7.8 Hz, 1 H, Ar), 6.80 (dd, J=7.8 and 1.2 Hz, 1 H, Ar), 6.70 (dt, J=7.8 and 1.2 Hz, 1 H, Ar), 6.06 (ddt, J=17.4 and 10.5 and 7.8 Hz, 1 H, HC=C), 5.52 (dd, J=17.4 and 1.8 Hz, 1 H, HC=C), 5.31 (dd, J=10.5 and 1.2 Hz, 1 H, HC=C), 4.59 (dt, J=4.8 and 1.5 Hz, 2 H, $CH_2$); $^{13}C$ NMR ($CDCl_3$) δ 157.09, 139.51, 132.57, 129.35, 122.66, 117.59, 112.58, 86.72, 69.68; IR (neat) 582, 1477 $cm^{-1}$.

EXAMPLE 2

Preparation of 6-allyl-2-iodophenol 3

To a solution of compound 2 (7.0 g, 27 mmol) in 130 ml of hexane was added $MeAlCl_2$ (Aldrich, 1.0 M in hexane, 22 ml 22 mmol) dropwise at −20° C. After the reaction mixture was stirred for 2 hr. at −20° C. under nitrogen, the reaction was quenched by adding water (40 ml) and the mixture slowly warmed to room temperature with swirling. Ethyl acetate (30 ml) was added to the reaction mixture, then stirring was continued for 5 min. After separating phases, the organic phase was washed with water (30 ml) and brine (30 ml), then dried and concentrated. The residue was purified by flash chromatography with 15:1 hexane/EtOAc to give product 3: 4.9 g, 70% yield; $R_f=0.38$ (20:1 hexane/EtOAc); $^1$H NMR (CDCl$_3$) δ 7.51 (dd, J=1.2 and 7.8 Hz, 1 H, Ar), 7.07 (d, J=7.8 Hz, 1 H, Ar), 6.62 (t, J=7.8 Hz, 1 H, Ar), 5.98 (ddt, J=17.4 and 9.6 and 6.6 Hz, 1 H, HC=C), 5.37 (s, 1 H, OH), 5.12 (m, 1 H, HC=C), 5.07 (m, 1 H, HC=C), 3.43 (d, J=6.6 Hz, 2 H, CH$_2$); $^{13}$C NMR (CDCl$_3$) δ 152.60, 136.33, 136.01, 130.73, 126.81, 122.42, 6.22, 86.41, 35.56; IR (neat) 3487 (OH), 1593, 1234 cm$^{-1}$; LRMS m/z (relative intensity) 51.1 (34), 77.1 (47), 105.1 (58), 118.1 (41), 133.1 (42), 260.0 (M+, 100).

EXAMPLE 3

Preparation of Compound 4

To a solution of compound 3 (4.9 g, 18.7 mmol) and imidazole (3.2 g, 47.1 mmol) in 20 ml of DMF was added t-butyldimethylsilyl chloride (3.1 g, 20.5 mmol) dissolved in 15 mmol of DMF at room temperature under nitrogen. After mixture was stirred for 12 hr. at room temperature, it was extracted with hexane (50 ml×8). The hexane phase was concentrated and then flash chromatographed to give compound 4: 6.3 g, 90% yield; $R_f=0.52$ (hexane); $^1$H NMR (dd, J=7.8 and 1.8 Hz, 1 H, Ar), 7.11 (dd J=7.8 and 1.8 HZ, 1 H, Ar), 6.66 (t, J=7.8 Hz, 1 H, Ar), 5.86 (ddt, J=17.4 and 9.6 and 6.6 Hz, 1 H, C=CHCH$_2$), 5.08 (m, 2 H, H$_2$C=C), 3.39 (d, J=6.9 Hz, 2 H, CH$_2$), 1.06 (s, 9 H, t-BuSi), 0.331 (s, 6 H, SiMe$_2$).

EXAMPLE 4

Preparation of Compound 5

Ozone was passed through a solution of compound 4 (722 mg, 1.9 mmol) in 19 ml of methanol at −78° C. until the deep blue color persisted (about 15 min.). The reaction was flushed with nitrogen gas and 8 ml of CH$_3$SCH$_3$ was added at −78° C. The reaction mixture was then allowed to stir for 30 min. at −78° C., for 1 hr. at 0° C. and for another 30 min. at room temperature. The methanol solvent was evaporated under reduced pressure, and 60 ml of ether was then added to the residue. After the mixture was washed with water (10 ml) and brine (20 ml×2), it was dried and concentrated. Flash chromatography gave product 5: 638 mg, 83% yield; $R_f=0.63$ (3:1 hexane/EtOAc); $^1$H NMR (CDCl$_3$) δ 6 9.63 (t, J=2.1 Hz, 1 H, CHO), 7.74 (dd, J=8.1 and 1.5 Hz, 1 H, Ar), 7.09 (dd, J=7.5 and 1.5 Hz, 1 H, Ar), 6.72 (t, J=7.5 Hz, 1 H, Ar), 3.68 (d, J=2.1 Hz, 2 H, CH$_2$), 1.05 (s, 9 H, t-BuSi), 0.32 (s, 6 H, SiMe$_2$); $^{13}$C NMR (CDCl$_3$) δ 199.34, 153.92, 139.70, 131.54, 124.26, 123.81, 91.23, 46.16, 26.37, 18.85, −1.52.

EXAMPLE 5

Preparation of Compound 6

To a solution of (carboxymethylene)triphenylphosphorane (Aldrich, 3.88 g, 11.5 mmol) dissolved in 30 ml of CH$_2$Cl$_2$ was added dropwise at room temperature aldehyde 5 (3.57 g, 9.3 mmol) dissolved in 14 ml of CH$_2$Cl$_2$. After the reaction was stirred for 12 hr. at room temperature, it was concentrated in vacuo and purified by flash chromatography with 5:1 hexane/EtOAc to give ester 6: 3.52 g, 83% yield; $R_f=0.46$ (5:1 hexane/EtOAc); $^1$H NMR (CDCl$_3$) δ7.67 (dd, J=7.8 and 1.5 Hz, 1 H, Ar), 7.05 (dd, J=7.5 and 1.5 Hz, 1 H, Ar), 6.99 (dt, J=15.6 and 6.6 Hz, 1 H, HC=C), 6.66 (t, J=7.5 Hz, 1 H, Ar), 5.80 (d, J=15.6 Hz, 1 H, HC=C), 4.18 (q, J=7.2 Hz, 2 H, OCH$_2$), 3.53 (dd, J=6.9 and 1.5 Hz, 2 H, CH$_2$), 1.27 (t, J=7.2 Hz, 3 H, CH$_3$), 1.05 (s, 9 H, t-BuSi), 0.32 (s, 6 H, Me$_2$Si); $^{13}$C NMR (CDCl$_3$) δ 166.32, 153.31, 146.18, 138.75, 130.60, 129.52, 123.61, 122.93, 91.09, 60.36, 33.94, 26.42, 18.94, 14.32, −1.49.

EXAMPLE 6

Preparation of Compound 7

To a three neck flask equipped with a hydrogen-filled gas balloon were added α,β-unsaturated ester 6 (619 mg, 1.36 mmol), ethanol (20 ml), 2 N aqueous HCl (0.4 ml) and PtO$_2$ (Aldrich, 60 mg). The reaction was flushed with hydrogen gas using an aspirator, and then stirred for 1 hr. at room temperature under the hydrogen balloon pressure. After the reaction was neutralized with 3 N aqueous NaOH (0.27 ml), it was poured into 100 ml of ethyl acetate (EtOAc). The solution was washed with brine (50 ml, 25 ml) and concentrated in vacuo. The residue was purified by flash chromatography to give compound 7: 562 mg, 90% yield; $R_f=0.52$ (7:1 hexane/EtOAc); $^1$H NMR (CDCl$_3$) δ 7.62 (dd, J=7.8 and 1.5 Hz, 1 H, Ar), 7.10 (dd, J=7.8 and 1.5 Hz, 1 H, Ar), 6.64 (t, J=7.8 Hz, 1 H, Ar), 4.11 (q, J=7.2 Hz, 2 H, OCH$_2$), 2.66 (t, J=7.8 Hz, 2 H, CH$_2$), 2.27 (t, J=7.5 Hz, 2 H, CH$_2$), 1.88 (m, 2 H, CH$_2$), 1.25 (t, J=7.2 Hz, 3 H, CH$_2$), 1.04 (s, 9 H, t-BuSi), 0.32 (s, 6 H, SiMe$_2$).

EXAMPLE 7

Preparation of Compound 8

To a solution of compound 7 (2.85 g, 6.2 mmol) in 60 ml of THF at −78° C. was added n-Bu$_4$NF (Aldrich, 1.0 M in THF, 6.2 ml, 6.2 mmol). The reaction mixture was stirred for 1 hr. at −78° C., then allowed to warm to 0° C., and quenched by adding water (10 ml). The mixture was poured into 50 ml of ethyl acetate, and washed with water (25 ml) and brine (20 ml). The organic phase was dried and concentrated. The residue was purified by flash chromatography with 4:1 hexane/EtOAc to give compound 8: 2.02 g, 94% yield; R:=0.37 (5:1 hexane/EtOAc); $^1$H NMR (CDCl$_3$) δ 7.53 (dd, J=7.8 and 1.2 Hz, 1 H, Ar), 7.05 (dd, J=7.8 and 1.2 Hz, 1 H, Ar), 6.58 (t, J=7.8 Hz, 1 H, Ar), 6.18 (s, 1 H, OH), 4.15 (q, J=7.2 Hz, 2 H, CH$_2$), 2.69 (t, J=7.2 Hz, 2 H, CH$_2$), 2.36 (t, J=7.2 Hz, 2 H, CH$_2$), 1.91 (m, 2 H, CH$_2$), 1.27 (t, J=7.2 Hz, 3 H, CH$_2$); $^{13}$C NMR (CDCl$_2$) δ 174.15, 152.96, 136.44, 130.64, 128.05, 122.06, 86.28, 60.59, 33.28, 30.54, 24.68, 14.24; IR (neat) 3373 (OH), 2980, 2957, 1707 (C=O), 1445 cm$^{-1}$. HRMS m/z calculated for C$_{12}$H$_{15}$O$_3$I 334.00660, found 334.00617.

EXAMPLE 8

Preparation of Compound 9

To a dried flask was added Pd(PPh$_3$)$_4$ (18 mg, 0.016 mmol). To this was added compound 8 (264 mg, 0.79 mmol) in 2 ml of THF, and the reaction mixture was stirred in an ice-water bath. Cyclopentadiene monoepoxide (97 mg, 1.18 mmol) in 2 ml of THF was added dropwise at 0° C., and stirring was continued for 20 min. at this temperature and another 24 hr. at room temperature. The reaction mixture was concentrated. The residue was purified by flash chromatography with 2:1 hexane/EtOAc to give product 9: 235 mg, 1% yield; R$_2$=0.27 (2:1 hexane EtOAc); $^1$H NMR (CDCl$_3$) δ 7.58 (dd, J=7.8 and 1.5 Hz, 1 H, Ar), 7.15 (dd, J=7.8 and 1.5 Hz, 1 H, Ar), 6.77 (t, J=7.8 Hz, 1 H, Ar), 6.09 (m, 1 H, HC=C), 6.01 (m, 1 H, HC=C), 5.11 (m, 1 H, CHOAr), 4.68 (m, 1 H, CHOH), 4.12 (q, J=7.2 Hz, 2 H, OCH$_2$), 2.85 (m, 2 H), 2.60 (ddd, J=15.3 and 9.6 and 6.0 Hz, 1 H, CH$_2$ in cyclopentane), 2.30 (dt, J=1.8 and 6.9 Hz, 2 H), 2.06 (dt, J=14.7 and 3.9 Hz, 1 H, CH$_2$ in cyclopentane), 1.88 (m, 2 H), 1.25 (t, J=6.3 Hz, 3 H, CH$_2$), 0.88 (m, 1 H, OH); $^{13}$C NMR (CDCl$_2$) δ 173.69, 156.22, 138.09, 137.98, 136.65, 133.55, 130.56, 125.87, 92.45, 85.71, 74.97, 60.52, 41.28, 33.50, 30.86, 25.47, 14.28; IR (neat) 3350 (OH, 2959, 1720 (C=O), 1599, 1462, 1352 cm$^{-1}$; HRMS m/z calculated for C$_{17}$H$_{21}$O$_4$I 416.04847, found 416.04747.

EXAMPLE 9

Preparation of Compound 11

To a solution of compound 9 (70 mg, 0.17 mmol) in 1.7 ml of toluene were added compound 10 (279 mg, 0.67 mmol), prepared as disclosed by M. E. Jung et al., *Tetrahedron Lett.*, 23, 3851 (1982), and AIBN (Aldrich Chem. Co., 2.8 mg, 0.017 mmol). The resulting mixture was placed into an oil bath preheated to 90° C. and stirred for 12 hr. After cooling to room temperature, the mixture was purified by flash chromatography with 1:1 hexane/EtOAc to give product 11 as a yellow oil: 65 mg, 80% yield; R$_2$=0.32 (1:1 hexane/EtOAc); $^1$H NMR (CDCl$_2$) δ 6.93 (d, J=7.5 Hz, 1 H, Ar), 6.86 (d, J=7.5 Hz, 1 H, Ar), 6.84 (dd, J=16.2 and 9.6 Hz, 1 H, HC=C), 6.73 (t, J=7.5 Hz, 1 H, Ar), 6.19 (d, J=16.2 Hz, 1 H, C=CH), 5.38 (dd, J=7.5 and 6.3 Hz, 1 H, CHOAr), 4.28 (m, 1 H, CHOH), 4.09 (m, 2 H, OCH$_2$), 3.98 (t, J=8.7 Hz, 1 H), 2.86 (dt, J=3.9 and 9.6 Hz, 1 H), 2.66-2.43 (m, 4 H) 2.25 (m, 2 H), 2.17 (ddd, J=15.3 and 6.4 and 4.1 Hz, 1 H), 2.09 (d, J=5.7 Hz, 1 H), 2.02 (m, 1 H), 1.86 (m, 1 H), 1.59 (m, 3 H), 1.41-1.22 (m, 7 H), 0.88 (t, J=6.9 Hz, 3 H, CH$_2$); IR (neat) 3466 (OH), 2930, 1666 (C=O), 1372, 1456 cm$^{-1}$; HRMS m/z calculated for C$_{25}$H$_{34}$O$_5$ 414.24062, found 414.24080.

EXAMPLE 10

Preparation of compounds 12 (R=Et) and 13 (R=Et)

(1) Procedure A (via reduction of compound 11)

To a solution of LiAlH$_4$ (Aldrich, 0.91 ml, 1.0 M in THF, 0.91 mmol) was added ethanol (0.46 ml, 2.0 M in THF, 0.91 mmol) dropwise at room temperature. To this was added (S)-binaphthol (Aldrich, 258 mg, 0.91 mmol) in 1.5 ml of THF, and the resulting mixture was stirred for 30 min. Enone 11 (126 mg, 0.30 mmole) in 1.2 ml of THF was added dropwise over 3 min at −100° C. The resulting mixture was stirred for 2 hr at −100° C., and then another 2 hr at −78° C. Methanol (0.5 ml) was added at −78° C. to destroy the excess reducing agent and the mixture was allowed to warm to room temperature. After the addition of water (20 ml) and diethyl ether (25 ml), stirring was continued for 10 min. The solution was neutralized with 2 N aqueous HCl, and then extracted with ether (3×30 ml). The organic phase was dried over MgSO$_4$ and concentrated in vacuo. The crude product was purified by flash chromatography using 1:2 hexane/EtOAc to give compound 12 (R=Et) (11 mg, 9% yield) and compound 13 (R=Et) (52 mg, 41% yield) as an oil. Starting material 11 (14 mg, 11% yield) was also recovered.

Compound 12 (R=Et): R$_f$=0.17 (1:2 hexane/EtOAc); $^1$H NMR (CDCl$_3$) δ 6.92 (d, J=7.5 Hz, 2 H, Ar), 6.73 (t, J=7.5 Hz, 1 H, Ar), 5.69-5.67 (m, 2 H, HC=CH), 5.34 (t, J=7.2 Hz, 1 H, CHOAr), 4.20 (m, 1 H, CHOH), 4.15-4.07 (m, 3 H, OCH$_2$ and C=CCHOH), 3.90 (t, J=9.0 Hz, 1 H, CHAr), 2.79-2.71 (m, 1 H), 2.66-2.51 (m, 2 H), 2.38 (d, J=15.0 Hz, 1 H, CH$_2$ in cyclopentane), 2.27 (dt, J=1.5 and 7.2 Hz, 2 H), 2.15 (dt, J=15.0 and 5.4 Hz, 1 H, CH$_2$ in cyclopentane), pentane), 2.04-1 81 (m, 2 H), 1.63 (m, 4 H), 1.34 (m, 6 H), 1.25 (t, J=7.2 Hz, 3 H, CH$_2$), 0.92 (t, J=6.0 Hz, 3 H, CH$_3$); IR (neat) 3396 (OH), 2930, 1734 (C=O), 1458 cm$^-$; HRMS m/z calculated for C$_{25}$H$_{36}$O$_5$ 416.25627 found 416.25574.

Compound 13 (R=Et): R$_f$=0.38 (1:2 hexane/EtOAc); $^1$H NMR (CDCl$_3$) δ 6.96 (d, J=7.5 Hz, 1 H, AR), 6.91 (d, J=7.5 Hz, 1 H, Ar), 6.73 (t, J=7.5 Hz, 1 H, Ar), 5.69 (m, 2 H, HC=CH), 5.32 (t, J=7.5 Hz, 1 H, CHOAr), 4.14 (m, 1 H, CHOH), 4.07 (m, 3 H), 3.88 (t, J=9.3 Hz, 1 H), 2.74 (m, 1 H), 2.57 (m, 2 H), 2.35 (d, J=15.0 Hz, 1 H, CH$_2$ in cyclopentane), 2.27 (m, 2 H), 2.14 (dt, J=15.0 and 5.7 Hz, 1 H, CH$_2$ in cyclopentane), 1.99 (m, 1 H), 1.91-1.81 (m, 3 H), 1.49 (m, 2 H), 1.28 (m, 6 H), 1.24 (t, J=7.5 Hz, 3 H, CH:), 0.88 (t, J=6.6 Hz, 3 H, CH$_3$); IR (neat) 3443 (OH), 2987, 1732 (C=O), 1593, 1456 cm$^{-1}$; HRMS m/z calculated for C$_{25}$H$_{36}$O$_5$ 416.25627, found 416.25591.

(2) Procedure B (via direct conversion from compound 9)

In a vial were placed racemic compound 9 (100 mg, 0.24 mmol), optically active γ-stannyl allylic alcohol 14 (401 mg, 0.96 mmol) prepared as disclosed by M. Suzuki et al., *Tetrahedron*, 46, 4809 (1990), toluene (2.4 ml) and AIBN (Aldrich, 3.9 mg, 0.024 mmol). The reaction mixture was heated for 130° C. for 16 hr. The resulting mixture was cooled to room temperature, and purified by flash chromatography using 1:1 to 1:2 hexane/EtOAc to give optically active 12 (R=Et) (22 mg, 21% yield) and 15 (R=Et) (19 mg, 20% yield). The spectral data for this compound are the same as for the racemic mixture 13 (R=Et).

Preparation of (+)-5,6,7-trinor-4,8-inter-m-phenylene PGI$_2$ [12 (R=H)]

To a solution of compound 12 (R=Et) (40 mg, 0.10 mmol) in 1.2 ml of THF was added 0.6 ml of 3 N aqueous NaOH. After the reaction mixture was stirred for 4 days at room temperature, it was neutralized with 2 N aqueous HCl. The organic phase was decanted with ethyl acetate (3×5 ml), then dried over MgSO$_4$ and concentrated in vacuo. Flash chromatography with 20:1 EtOAc/MeOH gave the title product: 27 mg, 72% yield; R$_f$=0.21 (20:1 EtOAc/MeOH); $^1$H NMR (CDCl$_3$) δ 6.91-6.87 (m, 2 H, Ar), 6.70 (t, J=7.5 Hz, 1 H, Ar), 5.59 (m, 2 H, HC=CH), 5.29 (t, J=6.9 Hz, 1 H, CHOAr), 4.95 (br s, 2 H, OH's), 4.17 (m, 1 H, CHOH), 4.03-3.99 (m, 1 H, C=CH—CHOH), 3.84 (t, J=8.7 Hz, 1 H, CHAr), 2.75-264 (m, 2H), 2.57-2.48 (m, 1 H), 2.34 (d, J=15.3 Hz, 1 H, CH$_2$in cyclopentane), 2.25 (t, J=6.6 Hz, 2 H), 2.16-1.99 (m, 2 H), 1.88-1.76 (m, 1 H), 1.48 (m, 3 H), 1.31 (m, 6 H, CH$_2$'s), 0.91 (t, J=6.9 Hz, 3 H, CH$_3$). This compound has $^1$H NMR spectral data very close to those reported by K. Ohno et al., *Tett. Letters*, 31, 4489 (1990); $^{13}$C NMR (CDCl$_3$) δ 178.14, 158.02, 136.25, 128.87, 128.38, 127.64, 123.94, 122.75, 119.86, 88.30, 77.00, 73.03, 52.10, 49.87, 41.92, 36.89, 32.89, 31.80, 28.79, 25.24, 24.79, 22.72, 14.14; IR (neat) 3510 (OH), 2935, 1703 (C=O) cm ; HRMS m/z calculated for C$_{23}$H$_{32}$O$_5$ 388.22497, found 388.22530.

Preparation of compound 15 (R=H)

To a solution of compound 15 (R=Et) (37 mg, 0.09 mmol) in 1.2 ml of THF was added 0.6 ml of 3 N aqueous NaOH. After the reaction mixture was stirred for 4 days at room temperature, it was neutralized with 2 N aqueous HCl. The organic phase was decanted with EtOAc (3×5 ml), then dried over MgSO$_4$ and concentrated in vacuo. Flash chromatography with 20:1 EtOAc/MeOH gave compound 15 (R=H): 26 mg, 74% yield; R$_f$=0.29 (20:1 EtOAc/MeOH); $^1$H NMR (CDCl$_3$) δ 6.94 (d, J=7.5 Hz, 1 H, Ar), 6.91 (d, J=7.5 Hz, 1 H, Ar), 6 73 (t, J=7.5 Hz, 1 H, Ar), 5.71 (dd, J=15.6 and 5.4 Hz, 1 H, HC=C), 5.64 (dd, J=15.6 and 7.8 Hz, 1 H, C=CH), 5.31 (m, 1 H, CHOAr), 4.80 (br s, 2 H, OH's), 4.18 (m, 1H, CHOH), 4.10 (dd, J=11.7 and 6.3 Hz, 1 H, C=CCHOH), 3.88 (t, J=5.4 Hz, 1 H, CHAr), 2.77 (m, 1 H), 2.67 (m, 1 H), 2.55 (m, 1 H), 2.35 (d, J=15.0 Hz, 1 H, CH$_2$ in cyclopentane), 2.29 (dt, J=3.0 and 7.2 Hz, 2 H), 2.15 (dt, J=15.0 and 5.7 Hz, 1 H, CHz in cyclopentane), 2.06 (m, 1 H), 1.84 (m, 1 H), 1.49 (m, 3 H), 1.29 (m, 6 H), 0.89 (t, J=6.9 Hz, 3 H, CH$_3$); $^{13}$C NMR (CDCl$_3$) δ 178.17, 157.94, 136.42, 128.99, 127.66, 126.78, 124.19, 122.78, 119.98, 88.03, 76.97, 72.48, 52.31, 49.96, 42.16, 37.27, 33.01, 31.83, 29.02, 25.21, 24.66, 22.67, 14.18; IR (neat) 3362 (OH), 2926, 2851, 1701 (C=O), 1593, 1454 cm$^{-1}$; HRMS calculated for C$_2$H$_{25}$O$_5$ 388.22497, found 388.22512.

All patents, patent documents and publications cited herein are incorporated by reference herein, as though fully set forth.

The invention has been described with reference to various specific and preferred embodiments and techniques. However, it should be understood that many variations and modifications may be made while remaining within the spirit and scope of the invention.

What is claimed is:

1. A method for preparing benzoprostacyclins comprising reacting a compound of the general formula (III):

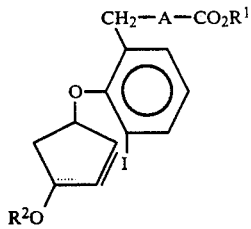

wherein R$^1$ is a pharmaceutically-acceptable cation, H or (C$_1$-C$_{12}$)alkyl; A is —CH$_2$—, —O—CH$_2$—, —CH$_2$—CH$_2$— or —CH=CH—; and R$^2$ is H, (C$_1$-C$_{12}$)alkyl, (C$_1$-C$_{10}$)acyl or (C$_7$-C$_{13}$)aroyl with a compound of a general formula (IV):

R$^7$—CH=CH—C(O)—CH(R$_4$)—B—R$_5$ (IV)

wherein R$^5$ is (C$_2$-C$_5$)alkyl; B is —(CH$_2$)$_n$—Z wherein n is 0-4 and Z is —CH$_2$CH$_2$—, —CH=CH— or —C≡C—; R$^4$ is H, F, CH$_3$ or CH$_2$CH$_3$; and R$^7$ is ((C$_1$-C$_4$)alkyl)$_3$Sn or (phenyl)$_3$Sn wherein the reaction is carried out in the presence of a catalytic amount of a free radical initiator to yield a compound of the formula (II):

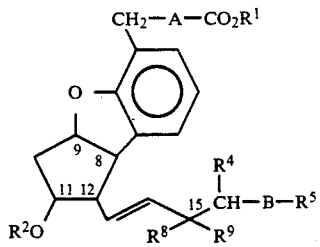

wherein R$^8$ and R$^9$ taken together are keto, and R$^1$, A, R$^2$, B and R$_5$ are as defined above.

2. The method of claim 1, further comprising reducing the C$_{15}$-keto group of compound II with a reducing agent to yield a compound of formula II wherein R$^8$ is H and R$^9$ is OH.

3. A method for preparing benzoprostacyclins comprising reacting a compound of the general formula (III):

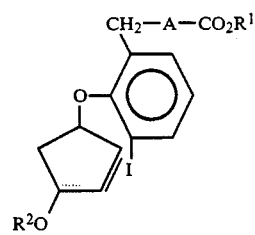

wherein R$^1$ is a pharmaceutically acceptable cation, H or (C$_1$-C$_{12}$)alkyl; A is —CH$_2$—, —O—CH$_2$—, —CH$_2$—CH$_2$— or —CH=CH—; and R$^2$ is H, (C$_1$-C$_{12}$)alkyl, (C$_1$-C$_{10}$)acyl or (C$_7$-C$_{13}$)aroyl with a compound of a general formula (V):

R$^7$—CH=C(R$^8$)(OR$^3$)—CH(R$_4$)—B—R$^4$ (V)

wherein R$^5$ is (C$_2$-C$_5$)alkyl; B is —(CH$_2$)$_n$—Z wherein n is 0-4 and Z is —CH$_2$CH$_2$—, —CH=CH— or —C≡C—; R$^4$ is H, F, CH$_3$ or CH$_2$CH$_3$; and R$^7$ is ((C$_1$-C$_4$)alkyl)$_3$Sn or (phenyl)$_3$Sn, R$^8$ is (C$_1$-C$_{12}$)-alkyl or H; and R$^3$ is H, (C$_1$-C$_{12}$)alkyl, (C$_1$-C$_{10}$)acyl or (C$_7$-C$_{13}$)aroyl; wherein the reaction is carried out in the presence of a catalytic amount of a free radical initiator to yield a compound of the formula (II):

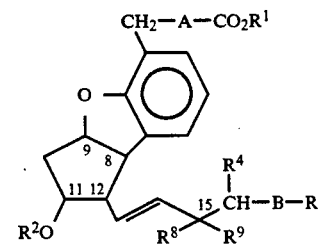

wherein R$^9$ is OR$^3$, and R$^1$, A, R$^2$, R$^3$, R$^4$, B, R$^5$ and R$_8$ are as defined above.

4. The method of claims 1 or 3 wherein R$^7$ is (n-butyl)$_3$Sn.

5. The method of claim 3 wherein R$^3$ is H in compounds II and V.

6. The method of claims 2 or 3 wherein compound II comprises (S)C$_{15}$—OH.

7. The method of claim 6 wherein the $C_{11}$—$OR^2$ bond is in the alpha-configuration.

8. The method of claim 1 wherein, in compound III, $R^1$ is $(C_1-C_{12})$alkyl and $R^2$ is H.

9. The method of claims 2 or 3 further comprising saponifying the $CO_2R^1$ moiety of compound II and neutralizing the reaction mixture to yield $CO_2H$.

10. The method of claim 9 further comprising forming a pharmaceutically acceptable alkali metal salt, ammonium, or amine salt of the moiety $CO_2H$.

11. The method of claims 1 or 3 wherein the free radical initiator is AIBN.

12. The method of claim 1 wherein the reaction is carried out in solution in an organic solvent.

13. The method of claim 2 wherein the reaction is carried out at about 50°–150° C.

14. The method of claim 13 wherein the reaction is carried out for about 5–48 hours.

15. The method of claim 1 wherein the mole ratio of III:IV is about 1:1.25–20.

16. The method of claim 1 wherein A is —$CH_2$— or —$CH_2$—$CH_2$— and B is $CH_2$—$CH_2$—$CH_2$.

17. The method of claim 16 wherein $R^4$ is H and $R^5$ is $CH_3$.

* * * * *